United States Patent
Nolte

(10) Patent No.: US 10,168,296 B2
(45) Date of Patent: Jan. 1, 2019

(54) FIELD-EFFECT TRANSISTOR AND METHOD AND CONTROL UNIT FOR OPERATING A FIELD-EFFECT TRANSISTOR

(71) Applicant: Robert Bosch GmbH, Stuttgart (DE)

(72) Inventor: Philipp Nolte, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 259 days.

(21) Appl. No.: 15/098,127

(22) Filed: Apr. 13, 2016

(65) Prior Publication Data
US 2016/0305904 A1 Oct. 20, 2016

(30) Foreign Application Priority Data
Apr. 14, 2015 (DE) .................. 10 2015 206 631

(51) Int. Cl.
*G01N 27/414* (2006.01)
(52) U.S. Cl.
CPC .................. *G01N 27/4141* (2013.01)
(58) Field of Classification Search
None
See application file for complete search history.

(56) References Cited

U.S. PATENT DOCUMENTS

| | | | |
|---|---|---|---|
| 2003/0038124 A1* | 2/2003 | Krieger | B60R 16/0238 219/209 |
| 2005/0057159 A1* | 3/2005 | Abiko | H01J 23/34 315/39.3 |
| 2007/0278098 A1* | 12/2007 | Yokosawa | G01N 27/4141 204/431 |
| 2011/0056926 A1* | 3/2011 | Coursey | B01L 7/525 219/490 |

* cited by examiner

*Primary Examiner* — Melissa Koval
*Assistant Examiner* — Nasima Monsur
(74) *Attorney, Agent, or Firm* — Maginot, Moore & Beck LLP

(57) ABSTRACT

A field-effect transistor includes a source electrode, a drain electrode, and a control electrode. The control electrode is configured as a heating unit having two terminals for receiving a heating voltage for heating the control electrode. The heating unit is configured as a meander-type heating element. A current-measuring device is configured to detect a current flowing between the source electrode and the drain electrode.

14 Claims, 5 Drawing Sheets

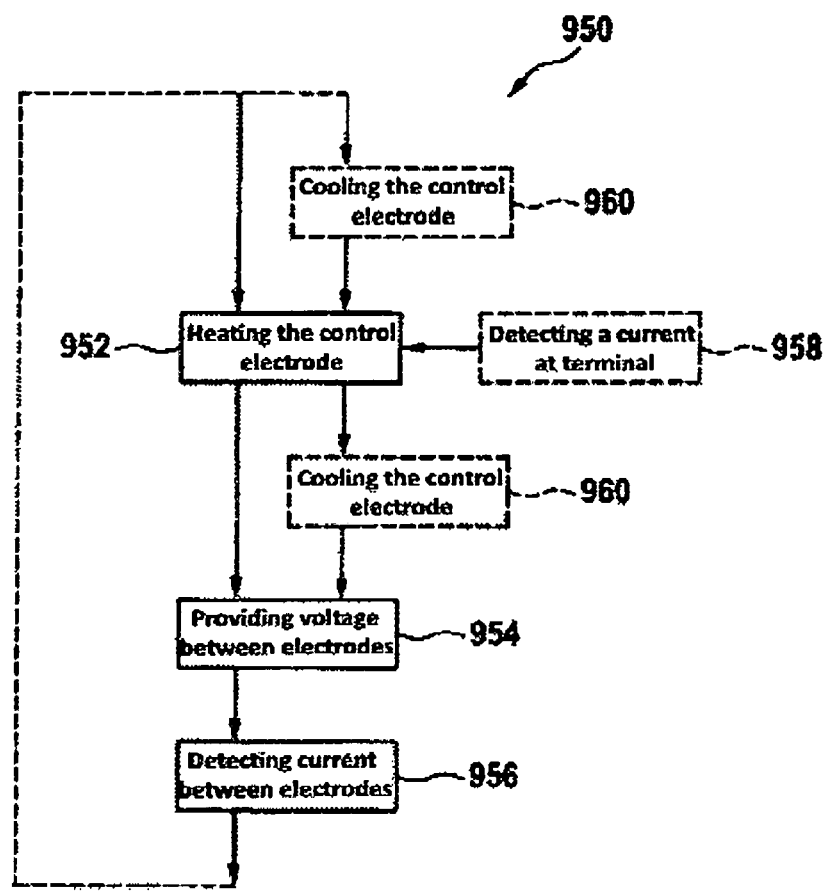

FIELD-EFFECT TRANSISTOR AND METHOD AND CONTROL UNIT FOR OPERATING A FIELD-EFFECT TRANSISTOR

This application claims priority under 35 U.S.C. § 119 to patent application no. DE 10 2015 206 631.2, filed on Apr. 14, 2015 in Germany, the disclosure of which is incorporated herein by reference in its entirety.

BACKGROUND

The present disclosure relates to a field-effect transistor, a method for operating a field-effect transistor, a corresponding control unit, and a corresponding computer program.

ChemFETs are field-effect transistors or transistors, the gate electrode of which is exposed to a gas in a carrier gas that is intended to be measured. They are capable of measuring minute concentrations of substances (for example, in the range between ppb and several ppm) in gasses.

ChemFETs can require a long time (for example, several minutes) in some cases until the response to an established gas concentration has stabilized, both in the case of an increasing concentration and in the case of a decreasing concentration. The decisive factor therefore is the kinetics of adsorption and desorption of the gas, which is supposed to be detected, at the electrode.

In applications, however, the concentration can change more quickly than it takes for the signal to stabilize. For example, it can be desirable to measure the concentration of a gas once every second and the concentration can also change within a few seconds, whereas the sensor would have to be exposed to a constant concentration for approximately one minute in order to obtain a stable, stationary signal.

SUMMARY

Proceeding from this background, the approach presented here presents a field-effect transistor, a corresponding method for operating a field-effect transistor, and a control unit, which uses this method, and, finally, a corresponding computer program according to the main claims. Advantageous embodiments result from the particular dependent claims and the description that follows.

A special design of the control electrode and a dynamic sensor operating mode are proposed. As a result, gate materials can be used in applications and can deliver a reliable signal that is sufficiently fast for the application, although the characteristic waiting time for the stabilization of the stationary signal would last too long.

A dynamic operation in which a sensor or a field-effect transistor is regenerated repeatedly by heating and cooling is advantageous. An energy-saving solution for the continuous implementation of heating cycles makes it possible for the sensor to be used in products having a rechargeable battery/battery operation, e.g., mobile electronic devices.

A field-effect transistor is presented, which is characterized in that a control electrode of the field-effect transistor is designed as a heating unit having two terminals, in particular for heating the control electrode, in particular wherein the heating unit is designed as a meander-type heating element.

The field-effect transistor can be understood to be a sensor. The field-effect transistor comprises a source electrode, a control electrode, and a drain electrode. The control electrode can be referred to as a gate electrode. The heating unit can be designed, for example, as a meander-type heating element. The heating unit can also comprise, for example, a plurality of heating wires disposed in parallel. When a current flows through the heating unit, said heating unit can heat up due to an electrical resistance of the heating unit, i.e., a so-called heating resistance. The advantage of such an embodiment is a reduced demand for heat output, since it is not the entire field-effect transistor or ChemFET that is heated, but rather only the control electrode. As a result, less heating energy is required (as compared to heating the entire sensor or field-effect transistor), which is advantageous, in particular, in the case of battery-operated devices. In addition to the reduced energy demand, a faster switching between different temperatures (for example, between the measurement and the desorption of gasses) can be achieved.

In this case, a supply resistance of the control electrode can be less than the heating resistance of the heating unit. Therefore, a supply lead having the supply resistance can heat up to a lesser extent or not at all as compared to the heating unit. In this case, the heating unit can comprise two supply leads, wherein the two supply leads can have a comparable or identical supply resistance. A material of the heating unit can have a high temperature dependence such that the heating resistance of the heating unit can also be used simultaneously as a temperature detector.

Turns of the heating unit, which is designed as a meander-type heating element, can be structured or arranged with homogeneous spacing. Therefore, during operation as a control electrode, an electric field can largely correspond to that of a typical, planar electrode. Alternatively, heating wires of the heating unit, which are disposed in parallel, can be disposed with largely homogeneous and comparable spacing.

The heating unit can have an electrical resistance between 1 Ohm and 1 MOhm. In particular, the heating unit can have an electrical resistance between 1 Ohm and 1 kOhm. The electrical resistance of the heating unit can be adapted to an available voltage and target temperature/ambient temperature and to a time interval of a heating and cooling phase.

The field-effect transistor can be designed as a chemically sensitive field-effect transistor for measuring a concentration of a fluid, in particular of a gas and/or a liquid. A chemically sensitive field-effect transistor can be referred to as a ChemFET. The ChemFET can therefore be understood to be both a gas sensor and a liquid sensor.

The field-effect transistor can have a heating unit for heating the field-effect transistor. The field-effect transistor can therefore be heated, in particular, to a constant temperature above an ambient temperature. For example, the field-effect transistor or a sensor in which the field-effect transistor is disposed can be heated to a constant temperature of, for example, 35° C., in particular, 50° C. This is advantageous, since the field-effect transistor, as a semiconductor element, exhibits a dependence on temperature and, therefore, a temperature control to a temperature above the (potentially fluctuating) ambient temperature can result in signal stabilization.

A method is presented for operating a variant of a field-effect transistor presented here, wherein a control electrode of the field-effect transistor is designed as a heating unit having two terminals, in particular for heating the control electrode, wherein the method includes at least the following steps:

heating the control electrode, wherein a heating voltage is provided between the two terminals of the control electrode in order to heat the control electrode to a predetermined temperature;

providing a first voltage between a source electrode and a drain electrode of the field-effect transistor and providing a second voltage between the source electrode and the control electrode; and detecting a current between the source electrode and the drain electrode, wherein the current represents a measured variable of the field-effect transistor.

The problem addressed by the disclosure can also be solved quickly and efficiently by this variant embodiment of the disclosure in the form of a method.

The method can include a step of detecting a current signal at a terminal of the control electrode in order to detect a resistance of the heating unit and/or a temperature of the control electrode.

In the step of providing, the second voltage can be present at one terminal of the control electrode or, alternatively, at the two, short-circuited terminals of the control electrode.

The method can include a step of cooling the control electrode, wherein voltage is not present at the field-effect transistor or at the control electrode for a predetermined time period or until a predetermined temperature of the control electrode is reached. In particular, the step of cooling can be carried out between the step of heating and the step of providing and, additionally or alternatively, before the step of heating. As an alternative, the method can therefore have one or two cooling phases.

The steps of the method can be carried out cyclically (repeatedly). A fluid or a parameter thereof can therefore be sensed over a relatively long time period. Therefore, for example, the step of detecting can be carried out over a time period of one second and the steps of heating and cooling can likewise be carried out, in alternation, over a time period of one second.

The approach presented here furthermore creates a control unit, which is designed for carrying out, controlling, or implementing the steps of a variant of a method presented here in corresponding devices. The problem addressed by the disclosure can also be solved quickly and efficiently by this variant embodiment of the disclosure in the form of a control unit.

In the present case, a control unit can be understood to be an electrical device, which processes sensor signals and, depending thereon, outputs control and/or data signals. The control unit can comprise an interface, which can be designed as hardware and/or software. In a hardware-type design, the interfaces can be part of a so-called system ASIC, for example, which contains highly diverse functions of the control unit. It is also possible, however, that the interfaces are inherent, integrated switching circuits or at least partially consist of discrete components. In a software-type design, the interfaces can be software modules, which are present, for example, on a microcontroller next to other software modules.

Another advantage is a computer program product or a computer program having program code, which can be stored on a machine-readable carrier or storage medium such as a semiconductor memory, hard-disk storage, or an optical memory and is used for carrying out, implementing, and/or controlling the steps of the method according to one of the above-described embodiments, in particular when the program product or the program is carried out on a computer or a device.

BRIEF DESCRIPTION OF THE DRAWINGS

The approach presented here is described, by way of example, in greater detail in the following with reference to the attached drawings. In the drawings:

FIG. 9 shows a flow chart of a method according to one exemplary embodiment of the present disclosure.

DETAILED DESCRIPTION

Figure 1:
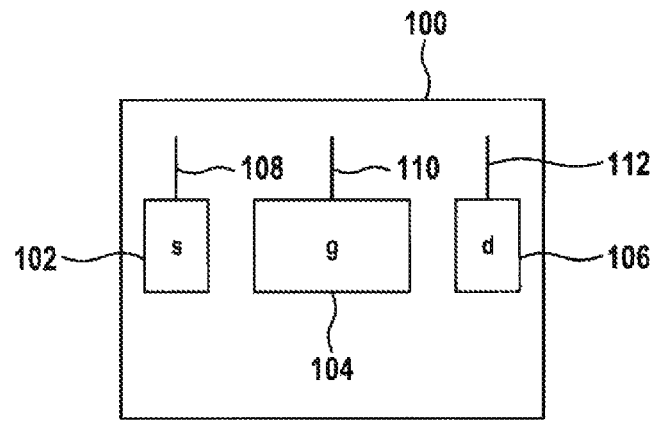
FIG. 1 shows a schematic depiction of a field-effect transistor.

In the following description of favorable exemplary embodiments of the present disclosure, the same or similar reference characters are used for the elements that are depicted in the various figures and act in a similar manner, wherein a description of these elements is not repeated.

FIG. 1 shows a schematic depiction of a field-effect transistor 100. In the case of the field-effect transistor 100 or FET 100, a type of charge is involved in the electric current—electrons or electron holes. The field-effect transistor can be, for example, a chemically sensitive field-effect transistor 100 or ChemFET 100. The field-effect transistor 100 comprises three electrodes 102, 104, 106, wherein a first electrode 102 is referred to as the source electrode 102 or source terminal 102, a second electrode 104 is referred to as the control electrode 104 or gate electrode 104, and a third electrode 106 is referred to as the drain electrode 106 or drain terminal 106. Each of the electrodes 102, 104, 106 has a terminal 108, 110, 112 or a supply lead 108, 110, 112, respectively. The terminals 108, 110, 112 can also be referred to as contacts 108, 110, 112. The source electrode 102 is electrically contactable via the first terminal 108, the control electrode 104 is electrically contactable via the second terminal 110, and the drain electrode 106 is electrically contactable via the third terminal 112. The control electrode 104 is preferably metallic (e.g., gold or platinum). However, it can be covered by an additional layer or layer system. This layer system can comprise, in particular, a single, gas-sensitive layer or a layer system, which contains, for example, metals, metal oxides, or organic crystal films. Since the gas-sensitive layer does not need to be changed as compared to a known FET having a conventional, non-heatable gate electrode, a more precise description of the sensitive layer will be omitted.

FIG. 1 shows a typical design of the electrodes 102, 104, 106 in a top view, wherein the control electrode 104 is designed so as to be planar and is provided with only one electrical contact 110 or supply lead 110.

Figure 2:
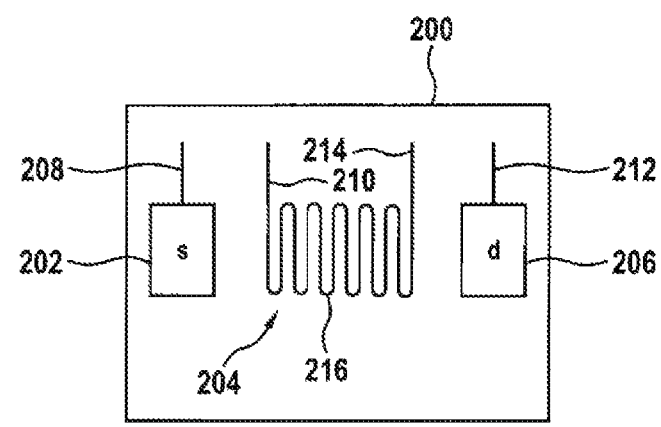
FIG. 2 shows a schematic depiction of a field-effect transistor according to one exemplary embodiment of the present disclosure.

FIG. 2 shows a schematic depiction of a field-effect transistor 200 according to one exemplary embodiment of the present disclosure. The field-effect transistor 200 comprises three electrodes 202, 204, 206, each having a terminal 208, 210, 212 assigned to an electrode 202, 204, 206, respectively. The depiction in FIG. 2 is similar to the depiction in FIG. 1, with the difference that the control electrode 204 comprises a second terminal 214 and the control electrode 204 between the two terminals 210, 214 is designed as a heating unit 216. In this case, the heating unit 216 is designed for heating the control electrode 204.

In the exemplary embodiment depicted, the heating unit 216 is designed as a meander-type heating element 216. Alternatively, the heating unit is formed, for example, by a plurality of heating wires disposed in parallel, similar to a rear-window heater in a passenger vehicle. Further variants, which convert a current flowing through the heating unit into heat energy, are possible.

FIG. 2 shows a variant of a design, according to the disclosure, of the gate electrode 204 in the form of a meander-type heating element 216 and having two electrical supply leads 210, 214.

In contrast to the exemplary embodiment depicted in FIG. 1, the control electrode 204 is designed in the form of a meander-type heating element 216 having two electrical supply leads 210, 214 instead of a single electrode 104 having a supply lead 110, as shown in FIG. 1.

The exemplary embodiment depicted in FIG. 2 provides for an alternating operation between a transistor function and a heater of the field-effect transistor 200 or the control electrode 204. The heating unit 216 is connected to a certain potential with respect to the source electrode 202 (this means that only one of the supply leads 210, 214 is used or, alternatively, is short-circuited). In the operation as a heater, an electrical voltage is applied between the two supply leads 210, 214.

As a result of lower heat capacities as compared to a heating of the entire field-effect transistor 200, it is possible to switch more quickly between different temperatures (for example, between the measurement and desorption of gasses).

As compared to the field-effect transistor depicted in FIG. 1, or a sensor that is completely heated, it is possible to switch more quickly between multiple, different temperatures, for example, in order to detect different substances using the same electrode, optionally in combination with evaluation methods, for example, main component analysis.

In one exemplary embodiment, a dynamic operating mode including complete regeneration permits a depiction of the adsorption kinetics at the electrode.

The field-effect transistor 200 can be the same material or material system as in a conventional ChemFET or field-effect transistor, with the difference that a structuring of the control electrode 204 in the sense of a meander-type heating element 216 and a second electrical contact 214 of the control electrode 204 is present.

Figure 7:
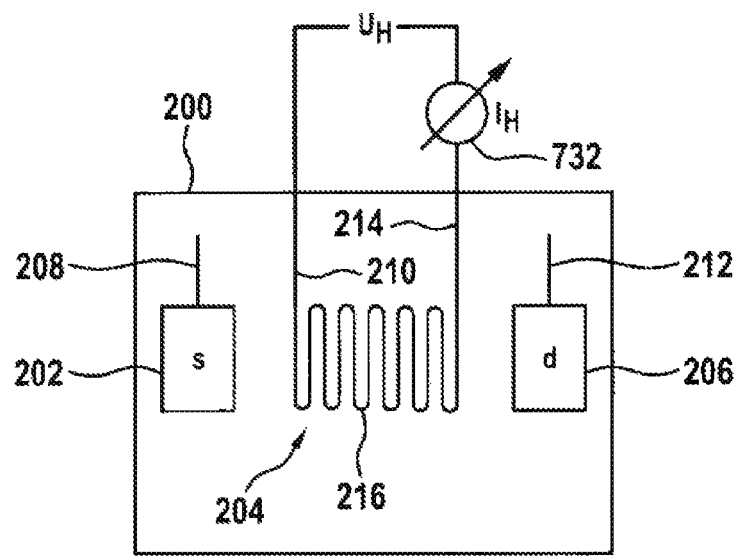

Particularly preferred in the design of the field-effect transistor are a supply resistance that is low as compared to a heating-meander resistance, and a high temperature dependence of the material used on the meander-type heating element, and so the heating resistance or heater resistance can also be used simultaneously as a temperature detector. This is shown in FIG. 7 by way of example.

It is advantageous that as many turns of the meander-type heating element 216 as possible are structured with homogeneous spacing, so that, during operation as a control electrode 204, the electric field largely corresponds to that of a typical, planar electrode.

For the effect as a heater, a low resistance (magnitude 1 Ohm to 1 kOhm) is desirable, and the design in this case depends on the available voltages and target temperature/ambient temperature. Since a stationary current should not flow between the source electrode 202 and the control electrode 204 (which is usually the case with a field-effect transistor), and, instead, only the application of a field is relevant, a high resistance is not critical, either. It merely needs to be ensured that the charges that are produced or that are present as a result of applying or changing the gate voltage can flow in or out accordingly.

The principle and the fundamental idea of the exemplary embodiment depicted in FIG. 2 also apply by analogy for other FET geometries, for example, for a suspended gate FET, in which the gate electrode is separated from the semiconductor region and the source/drain electrode by an air gap.

The exemplary embodiment depicted in FIG. 2 is intended primarily for measurements of gasses, although it can also be used in a corresponding manner for detecting substances in liquids.

The sensor 200 can also be equipped with another heater, which is not shown, or with a heating unit, which is not shown. In this case, the non-depicted heating unit is designed for heating the entire FET or sensor, for example, to 50° C. This is advantageous, since the field-effect transistor 200, as a semiconductor element, exhibits a dependence on temperature and, therefore, a temperature control to a temperature above the (potentially fluctuating) ambient temperature results in a signal stabilization. The heated control electrode 204 according to the disclosure is used only for locally heating the control electrode 204 to even higher temperatures.

Figure 3:
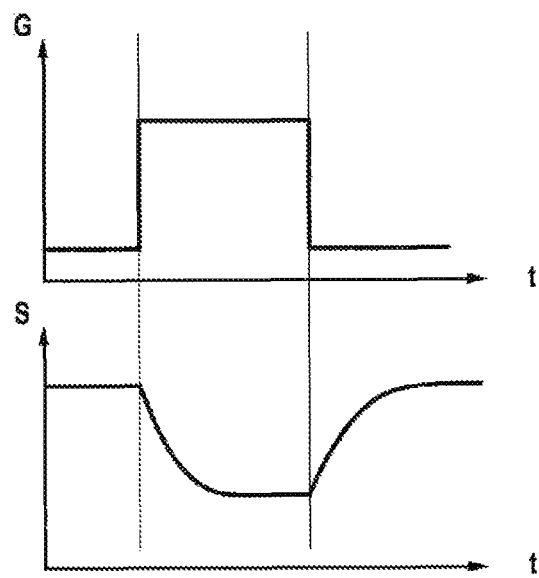
FIG. 3 shows a schematic depiction of sensor signals from chemically sensitive field-effect transistors according to one exemplary embodiment of the present disclosure.

FIG. 3 shows a schematic depiction of the sensor signal (lower partial sketch) in the case of a defined change in a gas concentration to be measured (upper partial sketch), of the type that can form during a constant operating temperature. It is essential that, at the sensor, the signal does not abruptly change to a stationary value, but rather requires a certain run-up time for the increase as well as the decrease in the concentration. This signal would be expected for a ChemFET at a constant temperature, which can also be achieved with the approach presented here, but which does not utilize the approach of a heating and an operating mode presented here.

Figure 4:
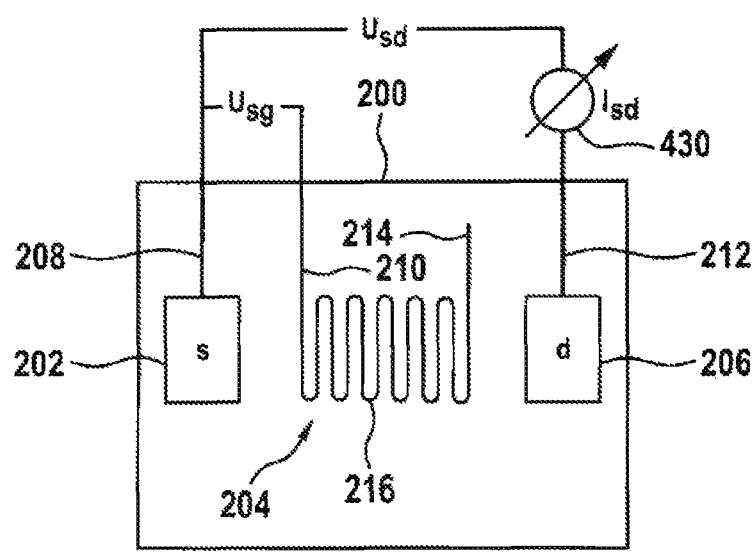
FIGS. 4 to 7 each show a schematic depiction of a field-effect transistor according to one exemplary embodiment of the present disclosure.
Figure 5:
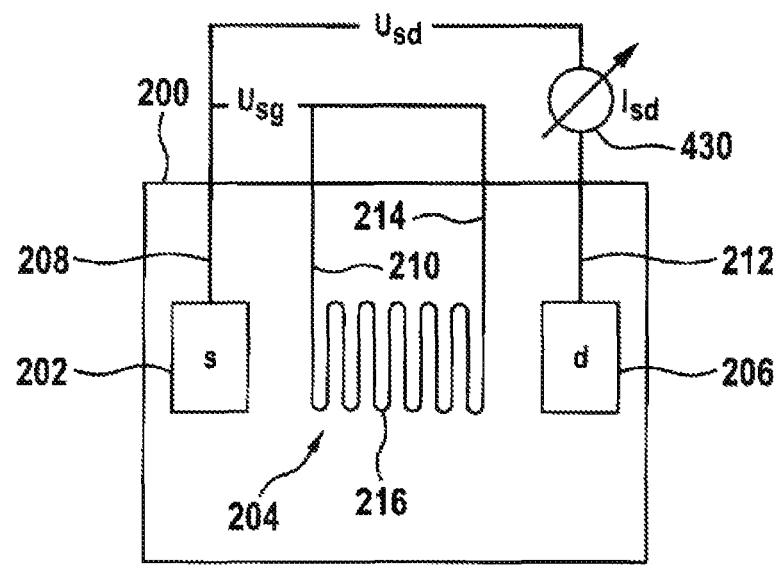
Figure 6:
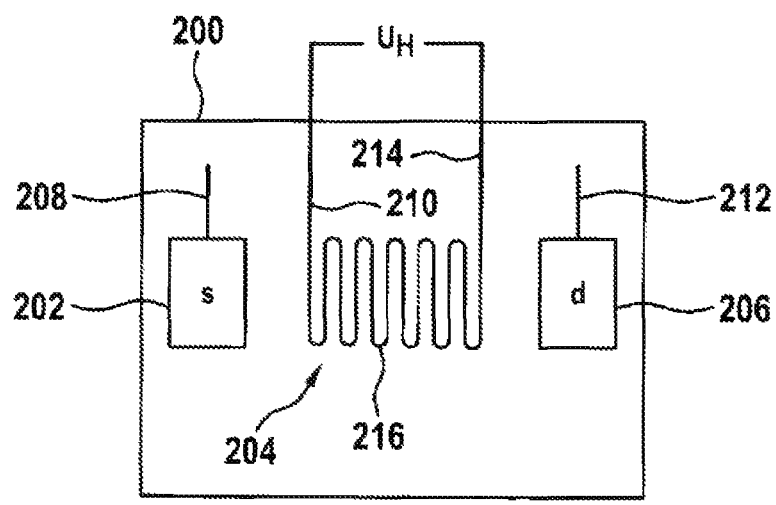

FIG. 4 and FIG. 5 show a wiring of the field-effect transistor 200 for a measuring mode, and FIG. 6 and FIG. 7 show a wiring of the field-effect transistor 200 for a heating mode. It is preferable to switch between the two modes. In principle, the combined, simultaneous mode is also possible, although the gate voltage or the control voltage is then no longer single-valued, but rather drops along the gate or the control electrode 204. This can be compensated for, however, by means of a suitable signal evaluation.

FIG. 4 shows a schematic depiction of a field-effect transistor according to one exemplary embodiment of the present disclosure. The field-effect transistor can be a variant of an exemplary embodiment of a field-effect transistor 200 shown in FIG. 2. This can be, for example, a chemically sensitive field-effect transistor 200. The depiction in FIG. 4 largely corresponds to the depiction in FIG. 2, with the difference that a first variant of a wiring during the measuring mode as a transistor is depicted. A voltage $U_{SD}$ is applied between the source electrode 202 and the drain electrode 206, and another voltage $U_{SG}$ is applied between the source electrode 202 and the control electrode 204, as is typical for a field-effect transistor. In this case, in the combined gate-heater electrode 200, either a contact 210 can be connected to the voltage source or the other contact 214 remains free, as is shown in FIG. 4. Alternatively, both contacts 210, 214 can also be short-circuited and connected to the voltage source, as is shown in FIG. 5. A current-measuring device 430, which is designed for determining the current $I_{SD}$ between the source electrode 202 and the drain electrode 206, is disposed at the terminal 212 of the drain electrode 206.

The control electrode 204 can be understood to be a self-heated gate electrode 204 on a ChemFET 200.

FIG. 5 shows a schematic depiction of a field-effect transistor 200 according to one exemplary embodiment of the present disclosure. The depiction in FIG. 5 largely corresponds to the depiction in FIG. 4, with the difference that the two contacts 210, 214 of the control electrode 204 are short-circuited and are connected to the voltage source.

FIG. 6 shows a schematic depiction of a field-effect transistor 200 according to one exemplary embodiment of the present disclosure. The field-effect transistor can be a variant of an exemplary embodiment of a field-effect transistor 200 shown in FIG. 2. This can be, for example, a chemically sensitive field-effect transistor 200. The depiction in FIG. 6 largely corresponds to the depiction in FIG. 2, with the difference that a voltage $U_H$ is applied between the two contacts 210, 214 of the control electrode 204. In a phase of heating, a voltage $U_H$ is applied at the combined gate-electrode-heater 204. In addition, the current can also be measured, in order to determine the resistance (or, alternatively, the resistance can be determined directly by means of a corresponding multimeter). The resistance measurement can be used for the temperature measurement. This is depicted accordingly in FIG. 7.

FIG. 7 shows a schematic depiction of a field-effect transistor according to one exemplary embodiment of the present disclosure. The depiction in FIG. 7 largely corresponds to the depiction in FIG. 6, with the difference that a current-measuring device 732 is disposed between the two contacts 210, 214 of the control electrode 204. In the exemplary embodiment, the heating resistance of the heating unit 216 is also used simultaneously as a temperature detector.

Figure 8:
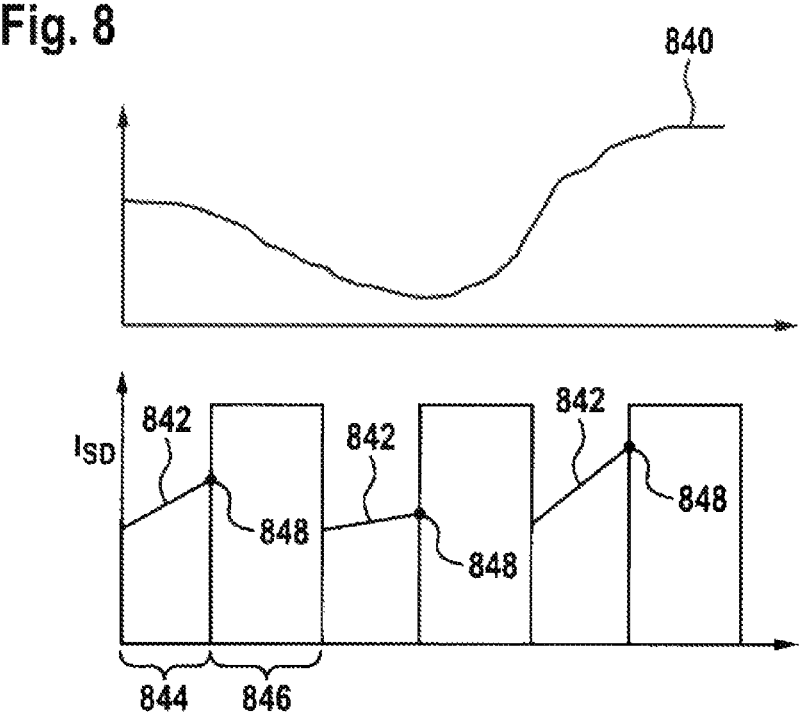
FIG. 8 shows a simplified depiction of a measuring cycle having a fluid concentration and a measured signal of a field-effect transistor according to one exemplary embodiment of the present disclosure.

FIG. 8 shows a simplified depiction of a measuring cycle having a fluid concentration and a measured signal of a field-effect transistor according to one exemplary embodiment of the present disclosure. Two Cartesian coordinate systems are depicted. In the upper coordinate system, time is depicted on the abscissa and a concentration of a fluid in a fluid mixture is depicted on the ordinate. The signal curve 840 shows a concentration of a fluid over time. In the lower coordinate system, time is likewise depicted on the abscissa and a current $I_{SD}$ is depicted on the ordinate. The current $I_{SD}$ is the current $I_{SD}$, for example, between the source electrode and the drain electrode, which is detected by the current-measuring device 430 depicted in FIG. 4. The two time axes correspond to one another, and so a concentration of the fluid depicted in the upper coordinate system can be assigned directly to a measured value 842 that is detected and is depicted in the lower coordinate system. A measuring phase 844 is followed by a heating and cooling phase 846, which is again followed, cyclically, by a measuring phase 844 and a heating and cooling phase 846, and so forth.

By way of example, the objective is to measure a varying concentration of a substance and to depict it as well as possible. This is achieved by regularly alternating between heating/cooling phases 846 and measuring phases 844. The end point 848 at the end of a measurement interval 844, or characteristic points of the transient course of the slope (for example, the mean value of the derivative of the measured signal), for example, can be used as a measure of the concentration.

The upper partial drawing schematically shows the course of the concentration of a substance to be detected. The lower partial drawing shows a sequence of measuring phases 844 and heating and cooling phases 846 (for example, the individual phases can last for 1 second). The signal of a ChemFET is depicted as lines 842. The ChemFET can be an exemplary embodiment of a field-effect transistor 200 depicted in FIG. 2 and in FIG. 4 through FIG. 7. The points 848 are the signal at the end of the measurement interval 844 and yield quantitative information regarding a low, middle, and high concentration. In addition, the transient signal 842 can be used for a further analysis.

FIG. 9 shows a flow chart of a method 950 according to one exemplary embodiment of the present disclosure. The method 950 for operating a field-effect transistor includes at least one step 952 of heating, one step 954 of providing, and one step 956 of detecting. The field-effect transistor can be a variant of a field-effect transistor 200 depicted in FIG. 2 and in FIG. 4 through FIG. 7. In this case, the field-effect transistor comprises three electrodes, wherein the control electrode is designed as a heating unit having two terminals. In the step 952 of heating, the control electrode is heated, wherein a heating voltage is provided between the two terminals of the control electrode in order to heat the control electrode to a predetermined temperature. In the step 954 of providing, a first voltage is provided between a source electrode and a drain electrode of the field-effect transistor and a second voltage is provided between the source electrode and the control electrode. In the step 956 of detecting, a current between the source electrode and the drain electrode is detected, wherein the current represents a measured variable of the field-effect transistor.

Parallel, in particular, to the step 952 of heating, in an optional step 958 of detecting, a current signal is detected at a terminal of the control electrode, in order to detect a resistance of the heating unit and/or a temperature of the control electrode. The detected temperature can be used as a correcting variable or a control variable in the step 952 of heating, in order to heat the control electrode to a predetermined temperature value and simultaneously monitor it.

In the step 954 of providing, the second voltage is provided at one terminal of the control electrode or, alternatively, at the two, short-circuited terminals of the control electrode.

Optionally, the method 950 comprises an optional step 960 of cooling the control electrode. In the step 960, voltage is not provided to the field-effect transistor for a predetermined time period or until a predetermined temperature of the control electrode has been reached. Therefore, the control electrode can cool again. Alternatively, the step of cooling can be carried out before the step 952 of heating or after the step 952 of heating and before the step 954 of providing. Alternatively, the step 960 of cooling is carried out both before the step 952 of heating and after the step 952 of heating.

The steps of the method 950 are carried out in one exemplary embodiment so as to be cyclically repeated. In this case, the steps 952 of heating, 958 of detecting, and 960 of cooling form a heating and cooling phase and the steps 954 of providing and 956 of detecting form a measuring phase. The heating and cooling phase and the measuring phase can last for a comparable duration or different time periods. This is also depicted in the approach in FIG. 8.

The exemplary embodiments that are described and are shown in the figures are selected merely by way of example. Different exemplary embodiments can be combined with one another completely or with respect to individual features. In addition, one exemplary embodiment can be supplemented with features of another exemplary embodiment.

Furthermore, the method steps presented here can be repeated and carried out in a sequence other than the described sequence.

If one exemplary embodiment has an "and/or" link between a first feature and a second feature, this should be read to mean that the exemplary embodiment according to one exemplary embodiment comprises both the first feature and the second feature and, according to another exemplary embodiment, comprises either only the first feature or only the second feature.

What is claimed is:

1. A field-effect transistor comprising:
a source electrode; a drain electrode; and a control electrode configured as a heating unit, the control electrode having two terminals for receiving a heating voltage, the heating voltage being configured to heat the control electrode; and
a current-measuring device configured to detect a current flowing between the source electrode and the drain electrode,
wherein a supply resistance of the two terminals of the control electrode is less than a heating resistance of the control electrode between the two terminals.

2. The field-effect transistor according to claim 1, wherein windings of the heating unit are configured as a meander-type heating element and are disposed with homogeneous spacing.

3. The field-effect transistor according to claim 1, wherein the heating unit has an electrical resistance between 1 Ohm and 1 MOhm.

4. The field-effect transistor according to claim 1, wherein the field-effect transistor is configured as a chemically sensitive field-effect transistor for measuring a concentration of a fluid.

5. The field-effect transistor according to claim 1, further comprising:
a further heating unit configured to heat the field-effect transistor to a constant temperature above an ambient temperature.

6. The field-effect transistor according to claim 1, wherein a first voltage is supplied between a source electrode and a drain electrode of the field-effect transistor and a second voltage is supplied between the source electrode and the control electrode.

7. A method for operating a field-effect transistor including a control electrode configured as a heating unit, the control electrode having two terminals for feeding a current through the control electrode for heating the control electrode, the method comprising:
heating the control electrode by supplying a heating voltage between the two terminals of the control electrode in order to heat the control electrode to a predetermined temperature;
supplying a first voltage between a source electrode and a drain electrode of the field-effect transistor and supplying a second voltage between the source electrode and the control electrode; and
detecting a current between the source electrode and the drain electrode, the detected current representing a measured variable of the field-effect transistor,
wherein a supply resistance of the two terminals of the control electrode is less than a heating resistance of the control electrode between the two terminals.

8. The method according to claim 7, further comprising:
detecting a current signal at a terminal of the two terminals of the control electrode, in order to detect a resistance of the heating unit and/or a temperature of the control electrode.

9. The method according to claim 7, wherein the second voltage is present at a terminal of the two terminals and/or the second voltage is present at the two terminals which have been short-circuited.

10. The method according to claim 7, further comprising:
cooling the control electrode, wherein voltage is not present at the field-effect transistor during the cooling for a predetermined time period or until a predetermined temperature of the control electrode is reached.

11. The method according to claim 10, further comprising:
cooling the control electrode before heating the control electrode or cooling the control electrode after heating the control electrode and before supplying the first and second voltages.

12. The method according to claim 10, wherein the method is carried out cyclically repeatedly.

13. The method according to claim 7, wherein a control unit is configured to carry out, implement, and/or control all steps of the method.

14. The method according to claim 7, wherein a non-transitory machine-readable storage medium includes a computer program stored thereon, the computer program including instructions that, when executed by a processor, enable the processor to carry out, implement, and/or control all steps of the method.

* * * * *